(12) United States Patent
Gridnev

(10) Patent No.: US 6,294,708 B1
(45) Date of Patent: Sep. 25, 2001

(54) ALPHA-METHYLSTYRENE DIMER DERIVATIVES

(75) Inventor: Alexei Alexeyevich Gridnev, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/245,521

(22) Filed: Feb. 5, 1999

Related U.S. Application Data

(60) Provisional application No. 60/074,322, filed on Feb. 11, 1998.

(51) Int. Cl.[7] ................................................. C07C 2/74
(52) U.S. Cl. .......................................... 585/406; 585/428
(58) Field of Search .................................... 585/406, 428

(56) References Cited

U.S. PATENT DOCUMENTS

| | | | |
|---|---|---|---|
| 4,526,945 | 7/1985 | Carlson et al. | 526/145 |
| 5,028,677 | 7/1991 | Janowicz | 526/329.7 |
| 5,324,879 | 6/1994 | Hawthorne | 585/511 |
| 5,362,813 | 11/1994 | Antonelli et al. | 525/286 |
| 5,587,431 | 12/1996 | Gridnev | 525/269 |

FOREIGN PATENT DOCUMENTS

| | | |
|---|---|---|
| 08 027043 | 1/1996 | (JP) . |
| 08 217702 | 8/1996 | (JP) . |

OTHER PUBLICATIONS

Yamada et al., Preparation of Polymers with Substituted Allyl End Group Using Dimer of α–Methylvinyl Monomer as Addition–Fragmentation Chain Transfer Agent at High Temperatures, *Journal of Polymer Science*, 32, 2745–2754, 1994.

Sawamoto et al., Cationic Oligomerization of Unsaturated Dimers of Styrene and ρ–Methylstyrene, *American Chemical Society*, 14, No.3, 467–471, 1981.

Guillot, Copolymerization with Depropagation: Experiment and Prediction of Kinetics and Properties of α–Methylstyrene/Methyl Methacrylate Copolymers. I. Solution Copolymerization, *Journal of Applied Science*, 65, 2297–2313, 1997.

*Primary Examiner*—Marian C. Knode
*Assistant Examiner*—Thuan D. Dang
(74) *Attorney, Agent, or Firm*—Sudhir G. Deshmukh

(57) ABSTRACT

The present invention relates to a method of making alpha-methylstyrene dimers by combining a cobalt catalyst, a free-radical initiator and an alpha-methylstyrene monomer, in an inert atmosphere, to form a mixture. The mixture is heated to a temperature in the range of 5° C. to 140° C. to form alpha methyl styrene dimers. The present invention also relates to the products produced by this inventive method.

27 Claims, 2 Drawing Sheets

ALPHA-METHYLSTYRENE DIMER DERIVATIVES

This Application claim benifit to Provisional Application 60/074,322 filed Feb. 11, 1998.

FIELD OF THE INVENTION

The present invention relates to alpha-methylstyrene dimers and derivatives thereof and to processes of making the same.

BACKGROUND OF THE INVENTION

Alpha-methylstyrene dimers (AMSDs) may be used as addition fragmentation chain transfer agents in processes of making polymers by free radical polymerization. During polymerization reactions, chain transfer agents may be added to propagating radicals and undergo fragmentation to create new radical forms. AMSDs, unlike some other chain transfer agents, are odorless, easy to handle, and do not cause discoloration or influence the stability of polymers. Additionally, they provide a method of molecular weight control, and AMSD containing functional groups such as hydroxyl, vinyl and amino groups enhance reaction with other functional groups so that polymers formed thereby may be considered telechelic. Telechelic polymers are macromolecules having chains of polymerized monomer comprising reactive functional groups at the terminal ends of the chains. Telechelic polymers are widely used in the synthesis of specialty polymers.

One method of making AMSDs is by the cationic method as described by Savamoto et. al., Macromolecules 14, 467 (1981). Though this method provides a fairly inexpensive method of making AMSDs, the method is unable to produced AMSD derivatives (i.e., AMSDs comprising at least one functional group on one or both rings). Alpha methylstyrene monomers including functional groups may be used as starting materials in cationic methods, but functional groups, such as isocyanato and amino groups, are deactivated by the acid used during these methods. In addition, a cationic process tends to provide low yields of AMSDs of which a substantial percentage exits as an "internal" isomer. Please see FIG. 1. Some commercially available preparations of AMSDs believed to be prepared by a cationic method contain about 7% by weight of AMSDs existing as an "internal" isomer. AMSDs existing as an "external" isomer (Please see FIG. 2) show significantly higher reaction rates when used in processes of addition chain transfer compared to "internal" isomers which are relatively inert in such processes.

Another method of making AMSDs is by the radical polymerization process. This process is described in Yamada, et al., Journal of Polymer Science, Part A, Polymer Chemistry, Vol. 32, 2745–2754 (1994), which discloses a method of producing alpha-methylstyrene dimers using benzylbis(dimethylglyoximato)(pyridine)cobalt(III) and a reaction temperature of 60° C. Unfortunately, the method produces low AMSDs yields. Research performed on the polymerization characteristics of alpha-methylstyrene monomers reveals that polymerization occurs until a ceiling temperature, is reached. Then the polymerization of alpha-methylstyrene monomers into polymeric products is inhibited above the ceiling temperature. Martinet et. al., Journal of Applied Polymer Science, Vol. 65, 2297–2313 (1997) reports an alpha-methylstyrene monomer polymerization ceiling temperature of 61° C.

SUMMARY OF THE INVENTION

The present invention provides a dimerization process for making alpha-methylstyrene dimers in high yields. The process comprises the following steps:

a) adding a cobalt chain transfer catalyst, a free-radical initiator and an alpha-methylstyrene monomer, in an inert atmosphere, to form a mixture;

b) heating the mixture to a temperature in the range of 65° C. to 140° C.; and c) forming alpha-methylstyrene dimers.

The dimerization process yields a solution that comprises greater than 20% by weight, and preferably greater than 50% by weight, of AMSDs.

The present invention also provides alpha-methylstyrene derivatives represented by the formula

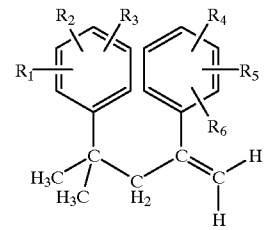

wherein $R^1$, $R^2$, $R^3$, $R^4$, $R^5$ and $R^6$ are each independently selected from group consisting of hydrogen, —CH(O), —CN, isocyanato, thioisocyanato, $SO_3H$ and salts and esters thereof, $NR^7R^8$, a silane, a halogen, —C(O)OR$^9$, —C(O)NR$^{10}$R$^{11}$, —CR$^{12}$(O), —C(O)OC(O)R$^{13}$, —C(O)NR$^{14}$COR$^5$, —OC(O)R$^{16}$, —OR$^{17}$, substituted and unsubstituted alkyl, substituted and unsubstituted alkenyl, substituted and unsubstituted alkynyl, and substituted and unsubstituted aryl; $R^7$, $R^8$, $R^9$, $R^{10}$, $R^{11}$, $R^{12}$, $R^{13}$, $R^{14}$, $R^{15}$, and $R^{16}$ are each independently selected from the group consisting of H, alkyl, aryl, substituted alkyl or substituted aryl; $R^{17}$ is selected from the group consisting of alkyl, aryl, substituted alkyl or substituted aryl; $R^1$, $R^2$, $R^3$, $R^4$, $R^5$ and $R^6$ cannot all simultaneously be hydrogen; and the alkyl and substituted alkyls have a chain consisting of 1 to 12 carbons.

As used herein, with respect to the present invention, the following shall apply:

"alpha-methylstyrene monomer" refers to alpha-methylstyrene monomer, derivatives thereof, or combinations of alpha-methylstyrene monomer and derivatives thereof, unless otherwise stated.

"derivatives" refer to alpha-methylstyrene monomers comprising one or more functional groups such as amino, isocyanato and hydroxyl groups, for example.

"alpha-methylstyrene dimer" or AMSD refers to a dimer prepared from alpha-methylstyrene monomers defined above.

BRIEF DESCRIPTION OF THE DRAWINGS

The present invention will be further explained with reference to the figures.

DETAILED DESCRIPTION OF THE INVENTION

Figure 1:
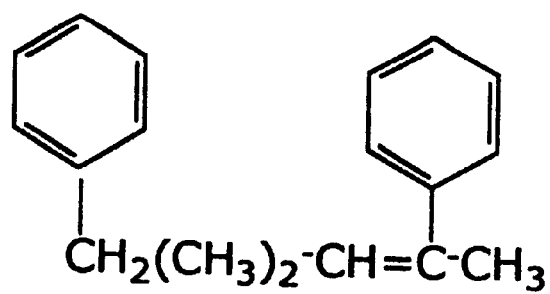
FIG. 1 illustrates an AMSD existing as an "internal" isomer.
Figure 2:
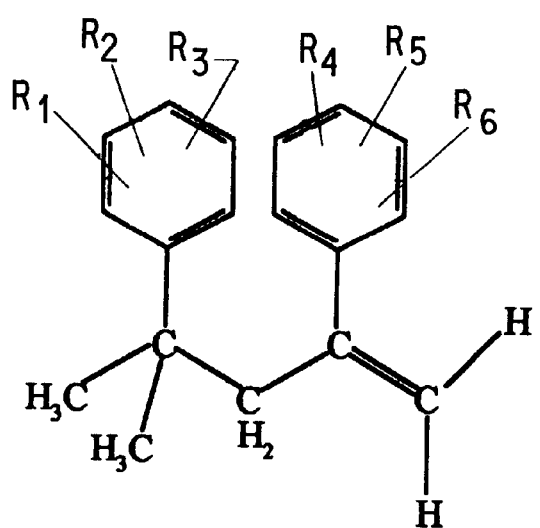
FIG. 2 illustrates an AMSD existing as an "external" isomer.

The present invention provides dimerization processes for making alpha-methylstyrene dimers in high yields using reaction temperatures in the range of 65° C. to 140° C., preferably in the range of 80° C. to 100° C. Because these dimerization processes do not involve cationic transfer, AMSDs, which include intact functional groups, are formed. In addition, most solutions prepared by the dimerization process of the present invention comprise less than 0.1% by weight of dimer existing as an "internal" isomer. FIG. 1 illustrates an AMSD existing as an "internal" isomer. For comparison purposes, FIG. 2 illustrates an AMSD existing as an "external" isomer. AMSDs in the form of "external" isomers are useful in further polymerization reactions, unlike AMSDs in the form of "internal" isomers.

The inventive dimerization process begins by combining, in an inert atmosphere, a cobalt catalyst, a free-radical initiator (generally an azo-initiator), an alpha-methylstyrene monomer and optionally other additives in a flask (e.g., solvent(s)). The resultant mixture is referred to as the reaction mixture. By "inert atmosphere" is meant an atmosphere substantially free of oxygen, generally provided by blanketing with nitrogen, argon, carbon dioxide, or other gas considered unreactive or inert with respect to reactants. Oxygen may be removed by freeze pump-thawing, flash vacuumation, or other methods known to those skilled in the art. The reactants are generally mixed, usually for a couple of minutes, before the heating step, to insure the catalyst and initiator are dissolved.

Preferred cobalt chain transfer catalysts for use in the practice of the present invention include cobalt (II) and cobalt (III) microcyclic chelates. Examples of such cobalt compounds and their structure are disclosed in Davis et al., J.M.S.-Rev. Macromol. Chem. Phys., C34(1), 243–324 (1994). Additional examples of such cobalt chain transfer catalysts are disclosed in U.S. Pat. No. 4,680,352 (Ittel et al.), U.S. Pat. No. 4,694,054 (Ittel et al.), U.S. Pat. No. 5,324,879 (Hawthorne et al.), WO 87/03605 (Hawthorne et al.) published Jun. 18, 1987, U.S. Pat. No. 5,362,826 (Antonelli et al.), and U.S. Pat. No. 5,264,530 (Antonelli et al.). Other useful cobalt compounds (cobalt complexes of porphyrins, phthalocyanines, tetraazoporphyrins, and cobaloximes) are disclosed in USSR Patent 664,434 (Enikolopov, N.S., et al.); USSR Patent 856,096 (Golikov, I., et al.); USSR Patent 871,378 (Belgovskii, I.M.); and USSR Patent 1,306,085 (Belgovskii, I.M., et al.). Examples of cobalt (II) and cobalt (III) chain transfer catalysts include, but are not limited to, those represented by the following structures:

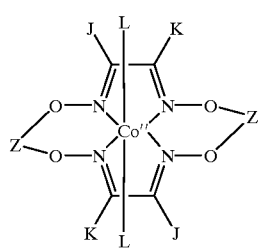

(1)

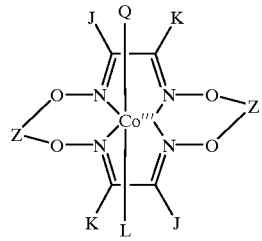

(II)

Referring to structures (I) and (II), Z can be hydrogen or $BR^{20}R^{21}$, where $R^{20}$ and $R^{21}$ are each independently selected from the group consisting of unsubstituted and substituted aryl, unsubstituted and substituted $C_1-C_{12}$ alkyl, unsubstituted and substituted $C_1-C_{12}$ alkoxy, unsubstituted and substituted aryloxy, and a halogen. Preferably Z is $BF_2$. J and K are preferably independently selected from the group consisting of phenyl, substituted phenyl, methyl, ethyl, or $—(CH_2)_4—$. L can be any one of a variety of neutral ligands commonly known in coordination chemistry and may be selected from the group consisting of water, amines, ammonia, and phosphines. Q is preferably an organic radical selected from the group consisting of isopropyl, 1-cyanoethyl, and 1-carbomethoxyethyl. Q may also be selected from the group consisting of alkyl, substituted alkyl or halogen. The catalysts can also include cobalt complexes of a variety of porphyrin molecules such as tetraphenylporphyrin, tetraanisylporphyrin, tetramesitylporphyrin and other substituted porphyrin species.

Regarding structure (I), some useful cobalt catalyst include:

| | |
|---|---|
| Co(II)(DPG-Z)$_2$, where | J = K = Phenyl (Ph), L = ligand |
| Co(II)(DMG-Z)$_2$, where | J = K = Methyl (Me), L = ligand |
| Co(II)(EMG-Z)$_2$, where | J = Me, K = Ethyl (Et), L = ligand |
| Co(II)(DEG-Z)$_2$, where | J = K = Et, L = ligand |
| Co(II)(CHG-Z)$_2$, where | J = K = $—(CH_2)_4—$, L = ligand |

Regarding structure (II), some useful cobalt catalyst include:

| | |
|---|---|
| QCo(III)(DPG-Z)$_2$, where | J = K = Ph, Q = alkyl, L = ligand |
| QCo(III)(DMG-Z)$_2$, where | J = K = Me, Q = alkyl, L = ligand |
| QCo(III)(EMG-Z)$_2$, where | J = Me, K = Et, Q = alkyl, L = ligand |
| QCo(III)(DEG-Z)$_2$, where | J = K = Et, Q = alkyl, L = ligand |
| QCo(III)(CHG-Z)$_2$, where | J = K = $—(CH_2)_4—$, Q = alkyl, L = ligand |
| QCo(III)(DMG-Z)$_2$, where | J = K = Me, Q = halogen, L = ligand |

DPG=diphenylglyoxime
DMG=dimethylglyoxime
EMG=ethylmethylglyoxime
DEG=diethylglyoxime
CHG=cyclohexylglyoxime The reaction mixture used in the inventive process may comprise from about 1 parts per million to 100 parts per thousand of catalyst and preferably in the range from about 100 parts per million to 10 parts per thousand. Cobalt catalyst are selected for use in a particular dimerization process, in part, based on factors such as solubility, monomer properties (e.g., polarity) and the like. One or more cobalt catalysts may be used in a dimerization process.

A free-radical initiator which produces carbon-centered radicals, sufficiently mild so as not to destroy the metal chelate chain transfer catalysts, is preferably employed in preparing AMSDs. Suitable initiators for use in the practice of the present invention are azo compounds having the requisite solubility and appropriate half life, including azocumene; 2,2'-azobis(2-methyl)-butanenitrile; 2,2'-azobis(isobutyronitrile)(AIBN); 4,4'-azobis(4-cyanovaleric acid); 2-(t-butylazo)-2-cyanopropane; 1,1'-azobis(cyclohexane-1-carbonitrile) and other compounds known to those skilled in the art.

A reaction mixture may comprise approximately 0.01% to approximately 10% by weight, preferably approximately 0.5% to approximately 3% by weight of azo-initiator. Azo-initiators are selected for a particular dimerization process, in part, based primarily on the recommended reaction temperature. One or more azo-initiators may be used in a dimerization process.

Figure 3:
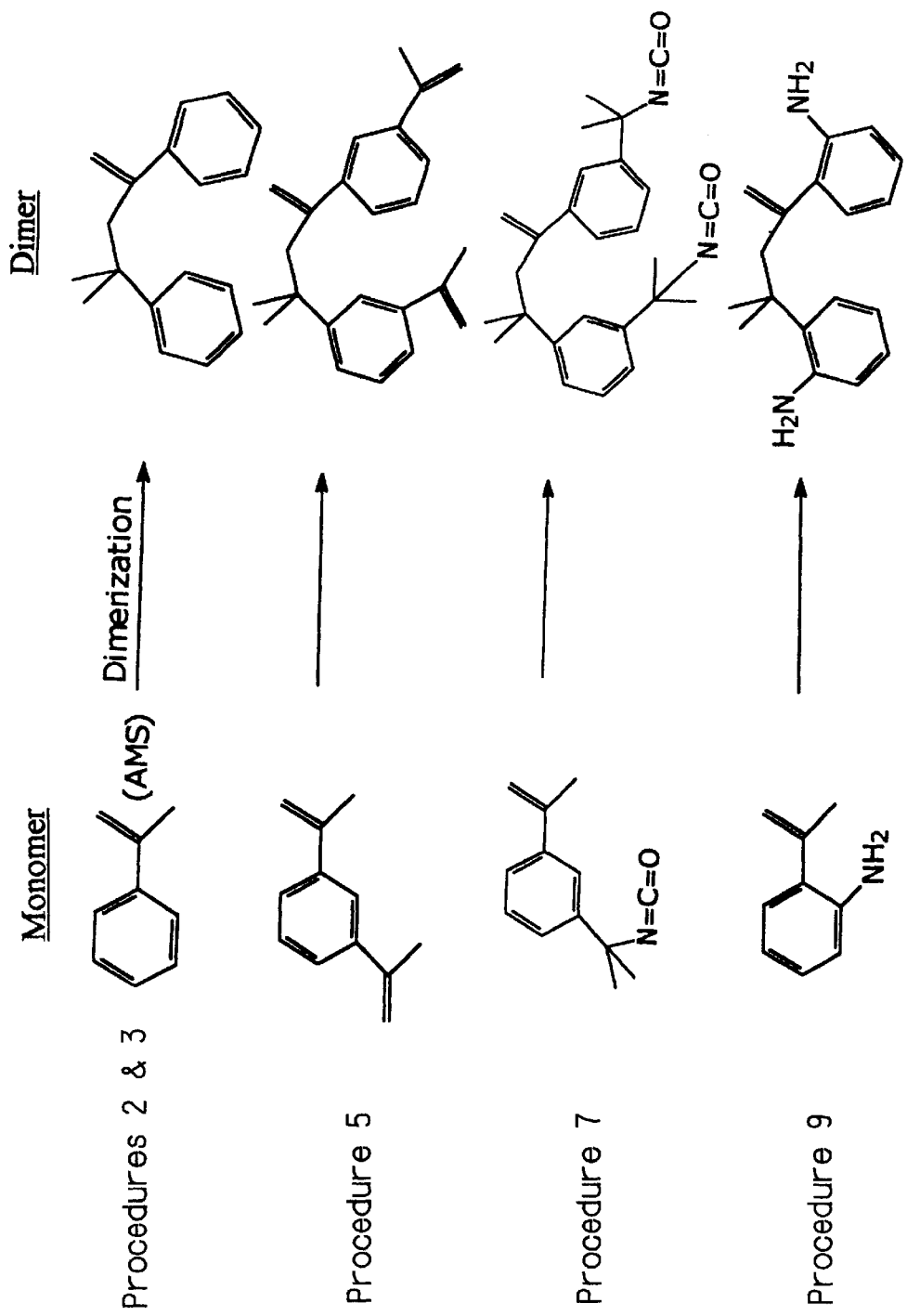
FIG. 3 illustrates the dimerization process of PROCEDURES 2, 3, 5, 7, and 9.

A reaction mixture also comprises alpha-methylstyrene monomers selected on the basis of the AMSDs to be formed. For example, an AMSD containing an isocyanate functional group may be prepared from an alpha-methylstyrene monomer comprising an isocyanate group. The preferred alpha-methylstyrene monomers used in the inventive process are those shown in FIG. 3. Each ring of an alpha-methylstyrene monomer may contain one or more functional groups. The functional groups located on each ring may be all the same, all different, or a combination of functional groups that are the same and that are different. A reaction mixture may comprise approximately 1% to approximately 100% by weight, preferably approximately 30% to approximately 100% by weight of alpha-methylstyrene monomer. One or more alpha-methylstyrene monomers may be used in a dimerization process.

The reaction mixture is heated to a reaction temperature in the range of approximately 65° C. to approximately 140° C., preferably in the range of 80° C. to approximately 100° C. The reaction mixture may be heated below 65° C., for example between 60° C. and 65° C. In some situations, an AMSD with an intact functional group may be prepared at low reaction temperatures if yield is not necessarily important. The reaction mixture may be heated by using a flame, oven or any other heating method that is known by one skilled in the art. The reaction mixture remains heated at the elevated temperature for at least 5 minutes up to 5 to 10 days, or even longer, depending upon the reactants used. Preferably the heating step has a duration in the range of approximately 30 minutes to approximately 12 hours and a solution comprising AMSDs is formed. Step heating may also be used in the inventive process wherein the reaction mixture is elevated to different temperatures for specified periods of time. Methods of initiating radical polymerization known by one skilled in the art may be used in the process of the present invention. The polymerization process may be initiated using an external source such as ultraviolet light, visible light, electron beam, or combinations thereof, for example. Initiating the polymerization process by heat is preferred.

The polymers made by the inventive process are typically prepared in a polymerization reaction by standard solution polymerization techniques, but may also be prepared by emulsion, suspension or bulk polymerization processes. The polymerization process can be carried out as either a batch, semi-batch, or continuous process (CSTR). When carried out in the batch process, the reaction mixture is prepared by combining monomer and metal chain transfer catalyst and adding this solution to a desired amount of initiator. Preferably the monomer-to-initiator ratio of the reaction mixture is 5 to 1000. The mixture is then heated for the requisite time, as described above. In a batch process, the reaction may be run under pressure to avoid monomer reflux.

As indicated above, the polymerization can be carried out in the absence of, or in the presence of, any medium or solvent suitable for free-radical polymerization, including, but not limited to, ketones such as acetone, butanone, pentanone and hexanone; alcohols such as isopropanol; amides such as dimethyl formamide; aromatic hydrocarbons such as toluene and xylene; ethers such as tetrahydrofuran and diethyl ether; ethylene glycol; dialkyl ethers, alkyl esters or mixed ester ethers such as monoalkyl ether-monoalkanoates; and mixtures of two or more solvents.

The solution formed, after the heating step, may comprise greater than 20% by weight, and preferably greater than 50% by weight, of AMSDs. A polymer solution may comprise, by weight percent, 20% to about 95% of AMSDs, preferably about 50% to about 95% of AMSDs. The polymer solution preferably comprises AMSDs in the form of "external" dimers with less than 0.1% (by weight) of the polymer solution comprising AMSDs existing as "internal" isomers. The free alpha-methylstyrene monomers not incorporated into dimers may be removed from the polymer solution by separation techniques well known in the art. The preferred separation technique is vacuum distillation, which removes unreacted monomer, solvent and other volatiles from the reaction products. AMSDs prepared according to the present invention can be used, not only as non-metallic chain transfer agents, but as components or intermediates in the production of graft copolymers, non-aqueous dispersed polymers, block copolymers, microgels, star polymers, branched polymers, and ladder polymers.

Alpha-methylstyrene derivatives produced may be represented by the formula

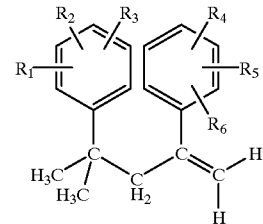

wherein $R^1$, $R^2$, $R^3$, $R^4$, $R^5$ and $R^6$ are each independently selected from group consisting of hydrogen, —CH(O), —CN, isocyanato, thioisocyanato, $SO_3H$ and salts and esters thereof, $NR^7R^8$, a silane, a halogen, $C(O)OR^9$, —C(O)$NR^{10}R^{11}$, —CR $^{12}$(O), —C(O)OC(O)$R^{13}$, —C(O)$NR^{14}COR^{15}$, —OC(O)$R^{16}$,—OR$^{17}$, substituted and unsubstituted alkyl, substituted and unsubstituted alkenyl, substituted and unsubstituted alkynyl, and substituted and unsubstituted aryl; $R^7$, $R^8$, $R^9$, $R^{10}$, $R^{11}$, $R^{12}$, $R^{13}$, $R^{14}$, $R^{15}$, and $R^{16}$ are each independently selected from the group H, alkyl, aryl, substituted alkyl or substituted aryl; $R^{17}$ is selected from the group alkyl, aryl, substituted alkyl or substituted aryl; $R^1$, $R^2$, $R^3$, $R^4$, $R^5$ and $R^6$ cannot all simultaneously be hydrogen. It is preferred that the alkyl and substituted alkyls have a chain consisting of 1 to 12 carbons. It is also preferred that substituents located on the substituted alkyl or substituted aryl are free of functionalities that could substantially interfere with free radical polymerization.

In addition, $R^1$, $R^2$, $R^3$, $R^4$, $R^5$ or $R^6$ may optionally form a cyclic structure selected from the group consisting of $C(O)OR^9$, —$C(O)NR^{10}R^{11}$, —$CR^{12}(O)$, —$C(O)OC(O)R^{13}$, —$C(O)NR^{14}COR^{15}$, —$OC(O)R^{16}$, —$OR^{17}$, substituted and unsubstituted alkyl, substituted and unsubstituted alkenyl, substituted and unsubstituted alkynyl.

Polymers may be prepared using alpha-methylstyrene dimers of the present invention, preferably using alpha-methylstyrene dimers as chain transfer agents. The methods used to prepare polymers of the present invention are those well known in the art such as radical polymerization or group transfer polymerization, for example. The polymers formed comprise at least one polymerized dimer of an alpha-methylstyrene derivative.

Chain transfer agents used in a polymerization process include methacrylate low oligomers, alpha-methylstyrene low oligomers, addition-fragmentation chain transfer agents, catalytic chain transfer agents (i.e., cobalt chelates, mercaptans, etc.), mercaptans, or combinations thereof. Other materials used to prepare polymers of the present invention include at least one ethylenically unsaturated monomer, such as, for example, alpha-methylene-gamma-butyrolactone and substituted alpha-methylene-ganma-butyrolactone, acrylic ester monomers including methyl acrylate, ethyl acrylate, butyl acrylate, 2-ethylhexyl acrylate, decyl acrylate, methyl methacrylate, butyl methacrylate, lauryl(meth)acrylate, isobornyl (meth)acrylate, isodecyl (meth)acrylate, oleyl(meth)acrylate, palmityl (meth)acrylate, stearyl(meth)acrylate, hydroxymethyl(meth)acrylate, hydroxyethyl (meth)acrylate, and hydroxypropyl (meth)acrylate; acrylamide or substituted acrylamides; styrene or substituted styrenes; butadiene; vinyl acetate or other vinyl esters; vinyl monomers, such as, for example, vinyl chloride, vinylidene chloride, N-vinyl pyrrolidone; amino monomers, such as, for example, N,N'-dimethylamino(meth)acrylate; and acrylonitrile or methacrylonitrile. Additionally copolymerizable ethylenically-unsaturated acid monomers in the range of, for example, from 0.1 percent to 7 percent, by weight based on the weight of the emulsion-polymerized polymer, acrylic acid, methacrylic acid, crotonic acid, itaconic acid, fumaric acid, maleic acid, monomethyl itaconate, monomethyl fumarate, monobutyl fumarate, maleic anhydride, 2-acrylamido-2-methyl-1-propanesulfonic acid, sodium vinyl sulfonate, and phosphoethyl methacrylate, may be used. Polymer prepared using AMSDs may be in the form of a solution or a dispersion of polymer particles.

The polymers of the present invention form a composition that may be used to prepare coatings. Polymer compositions of the present invention may include a substantially thermoplastic or substantially uncrosslinked polymer when applied to the substrate prior to the formation of a coating. A coating is formed when the polymer composition is hardened. Crosslinking or gelling of the polymer composition may be induced by adding to the monomer mix reactive diluents comprising ethylenically unsaturated groups and/or multi-ethylenically unsaturated monomers. Multi-ethyleneically unsaturated monomers preferably are in the range of 0.01% to 5%, by weight based on the weight of the polymer. Preferably multi-ethylenically unsaturated monomers include allyl methacrylate, trimethylolpropane triacrylate, diallyl phthalate, 1,4-butylene glycol dimethacrylate, 1,6-hexanedioldiacrylate and divinyl benzene. The multi-ethylenically unsaturated monomers are selected so that film formation is not materially impaired. Initiators used in the hardening process include conventional free radical initiators, such as, azo-initiators, hydrogen peroxide, benzoyl peroxide, t-butyl hydroperoxide, t-butyl peroctoate, ammonium, alkali persulfates and combinations thereof. Preferably the initiator is used in a concentration typically of 0.05% to 3.0% by weight, based on the weight of the polymer composition. Initiation may be enhanced by the use of external sources such as heat, ultraviolet light, electron beam or other sources known by one skilled in the art. The coatings of the present invention are preferably low VOC coating compositions. "Low VOC coating compositions" means a coating composition that includes less then 0.6 kilograms of organic solvent per liter (5 pounds per gallon) of the composition, as determined under the procedure provided in ASTM D3960. It is also preferred that the coatings of the present invention are a high solids composition. "High solid composition" means a coating composition having solid component of above 40 percent, preferably in the range of from 45 to 85 percent and more preferably in the range of from 50 to 65 percent, all in weight percentages based on the total weight of a polymer composition.

A coating composition containing the polymer prepared by the process of the present invention may also contain conventional additives, such as, reactive diluents, pigments, stabilizers, flow agents, toughening agents, fillers, durability agents, corrosion and oxidation inhibitors, rheology control agents, metallic flakes and other additives. Such additional additives will, of course, depend on the intended use of the coating composition. Fillers, pigments, and other additives that would adversely effect the clarity of the cured coating will not be included if the composition is intended as a clear coating.

The coatings of the present invention can be used as automotive coatings such as refinishes, primers, basecoats, undercoats, overcoats and clear coats. The polymers are also suitable for use in compositions for maintenance finishes for a wide variety of substrates, such as steel, copper, brass and aluminum or non-metallic substrates, such as, wood, leather, polymeric materials and concrete.

EXAMPLES

The examples below are carried out using standard techniques, which are well known and routine to those skilled in the art, except where otherwise described in detail. These examples are illustrative, but do not limit the invention. In all cases, the presence of the internal isomer was not detected, and is therefore assumed to be present at levels below 0.1 wt. %.

The freeze-pump-thaw cycle as used in the examples below is described in D.F. Shriver, et al., "The Manipulation of Air Sensitive Compounds", 2nd ed., Wiley Interscience, 1986.

$^1$H-NMR spectra were taken on a QE300 NMR spectrometer (General Electric Co., Freemont, Calif. 94539) at 300 MHz frequency.

Molecular weight (MW) and Degrees of Polymerization (DP) measurements were based on size exclusion chromatography (SEC) using styrene as a standard, and performed on a WISP 712 Chromatograph with 100 A, 500 A, 1000 A and 5000 A phenogel columns (Waters Corp., Marlborough, Mass.).

Unless otherwise specified, all chemicals and reagents were used as received from Aldrich Chemical Company, Milwaukee, Wis.

| DEFINITIONS | |
|---|---|
| VAZO-52 | 2,2"-azobis(2,4-dimethylvaleronitrile) (Dupont Co., Wilmington, DE) |
| VAZO-67 | 2,2'-azobis (2-methylbutyronitrile) (Dupont Co., Wilmington, DE) |
| VAZO-88 | 1,1'-azobis(cyclohexane-1-carbonitrile) (DuPont Co., Wilmington, DE) |
| AIBN | 2,2'-azobis(isobutyronitrile) |
| TAPCo | tetraanisylporphyrine-Co |
| HPCo | hemato-porphyrin-IX-Co tetramethyl ester |
| THPCo | [meso-tetrakis(4-heptyloxyphenyl)porphyrinato]cobalt(II) |
| COBF | [bis[m-(2,3-butanedione dioximato)(2-)-o,o']]tetrafluorodiborato(2-)-N,N', N",N"'](2-propyl)Co(III) (DuPont Co., Wilmington, DE) |

PROCEDURE 1

Procedure 1 is a dimerization process illustrating a reaction mixture free of a cobalt catalyst will not form AMSDs.

A reaction mixture was prepared in a 500 milliliter flask by combining 140 milliliters of alpha-methylstyrene (AMS) and a solution of 1.2 grams of VAZO-52 dissolved in 60 milliliters of acetone. The reaction mixture was degassed by three freeze-pump-thaw cycles. The flask containing the reaction mixture was immersed into 60° C. isothermal bath and incubated for 24 hours. An additional 0.6 grams of VAZO-52 was added followed by the degassing procedure described above. After degassing, the reaction mixture was incubated a second time at 60° C. for 24 hours and a solution was formed containing AMSDs. Approximately 1 milliliter of the solution was analyzed by both Nuclear Magnetic Resonance (NMR) and Size Exclusion Chromatography (SEC) indicating the sample was substantially free of alpha-methylstyrene dimer or higher oligomer.

PROCEDURE 2

Procedure 2 is a dimerization process illustrating a low reaction temperature (60° C.) will yield decreased amounts (21.3 weight %) of AMSDs. Please observe FIG. 3.

The dimerization process described in PROCEDURE 1 was followed. However, an additional component, 80 milligrams of COBF was added to the reaction mixture. After the second incubation, the solution was placed under a high vacuum (approximately 0.5 torrs) to remove acetone and residual monomer. Approximately 1 milliliter of the solution comprising AMSDs was analyzed by both NMR and SEC revealing that the sample was substantially free of trimers and higher oligomers. About 30 grams (21.3 weight %) of pure AMSD was prepared with the remainder of the solution comprising monomers.

PROCEDURE 3

Procedure 3 is a dimerization process illustrating elevated reaction temperatures (90° C.) will yield elevated amounts (48 weight %) of AMSDs. Please observe FIG. 3.

A reaction mixture was prepared in a 500 milliliter flask by combining 180 milliliters of AMS, 120 milligrams of COBF and a solution of 2 grams of VAZO-88 dissolved in 25 milliliters of acetone. The reaction mixture was degassed by flash-vacuumation (i.e., the flask was attached to a vacuum line for 2 minutes). The flask containing the reaction mixture was immersed into a 90° C. isothermal bath and incubated for 24 hours. The temperature was raised to 95° C. and the reaction mixture was incubated a second time for 24 hours. Upon completion of the second incubation, a solution containing AMSDs was formed and placed under a high vacuum (approximately 0.05 torr) to remove both acetone and residual monomer. Approximately 1 milliliter of the solution comprising AMSDs was analyzed by both NMR and SEC revealing the solution was substantially free of trimers and higher oligomers. About 86 grams (48 weight percent of the solution) of AMSDs were prepared and the remainder of the solution was substantially monomer.

PROCEDURE 4

Procedure 4 is a dimerization process illustrating a reaction mixture free of a cobalt catalyst will not form AMSDs.

A reaction mixture was prepared in a 500 milliliter flask by combining 10 milliliters of meta-diiso-propenylbenzene (m-DIPB) and a solution of 50 milligrams of VAZO-67 dissolved in 3 milliliters of dichloroethane. The reaction mixture was degassed by flash-vacuumation for 2 minutes. The flask containing the reaction mixture was immersed into a 65° C. isothermal bath and incubated for 48 hours to form a solution containing AMSDs. Approximately 1 milliliter of the solution was analyzed by both NMR and SEC revealing that the solution was substantially free of AMSDs.

PROCEDURE 5

Procedure 5 is a dimerization process illustrating elevated reaction temperatures (65° C.) will yield elevated amounts (50 weight %) of AMSDs with intact vinyl functional groups. Please observe FIG. 3.

The dimerization process described in PROCEDURE 4 was followed. However, an additional component, 1.6 milligrams of COBF was added to the reaction mixture. After the incubation step, the solution was placed under a high vacuum (approximately 0.5 torrs) to remove acetone and residual monomer. Approximately 1 milliliter of the solution containing AMSDs was analyzed by both NMR and SEC revealing the solution was substantially free of trimers and higher oligomers. About 50% by weight of the solution was AMSDs and the rest of the solution was substantially monomers.

PROCEDURE 6

Procedure 6 is a dimerization process illustrating a reaction mixture free of a cobalt catalyst will not form AMSDs.

A reaction mixture was prepared in a 500 milliliter flask by combining 4 milliliters of 3-isopropenyl-alpha, alpha-dimethylbenzyl isocyanate and a solution of 80 milligrams of VAZO-88 dissolved in 4 milliliters of dichloroethane. The reaction mixture was degassed. The flask containing the reaction mixture was immersed in a 65° C. isothermal bath and incubated for 6 days to form a solution containing AMSDs. The solution was chilled and an excess of diethylamine was added to convert isocyanate groups into diethylurea. The polymer solution was placed under a high vacuum (approximately 0.05 torr) to yield white waxy crystals. Approximately 1 gram of the crystals were analyzed by both NMR and SEC revealing the crystals were substantially free of AMSDs.

PROCEDURE 7

Procedure 7 is a dimerization process illustrating elevated reaction temperatures (65° C.) will yield elevated amounts (75 weight %) of AMSDs with intact isocyanate groups. Please observe FIG. 3.

The dimerization process described in PROCEDURE 6 was followed. However, an additional component, 6 milligrams of TAPCo was added to the reaction mixture. Approximately 1 milliliter of a solution was formed containing AMSDs and the solution was analyzed by both NMR and SEC revealing the solution was substantially free of trimers and higher oligomers. The solution containing, by weight, about 75% AMSDs and the rest of the solution was substantially monomers.

PROCEDURE 8

Procedure 8 is a dimerization process illustrating a reaction mixture free of cobalt catalyst will not form AMSDs.

A reaction mixture was prepared in a 500 milliliter flask by combining 10 milliliters of ortho-isopropenylaniline, 10 milliliters of 1, 2-dichloroethane and 0.18 grams initiator VAZO-88. The reaction mixture was degassed by three freeze-pump-thaw cycles. The flask containing the reaction mixture was immersed in a 90° C. bath for 2 days to form a polymer solution containing AMSDs. Approximately 1 milliliter of the solution was analyzed by both NMR and SEC revealing the solution was substantially free of AMSDs.

PROCEDURE 9

Procedure 9 is a dimerization process illustrating elevated temperatures (90° C.) will yield AMSDs having intact amino functional groups. Please observe FIG. 3.

The dimerization process described in PROCEDURE 8 was followed. However, an additional compound, 7 milligrams of THPCo, was added to the reaction mixture. Upon completion of the incubation step, a solution containing AMSDs was formed and placed under a high vacuum (approximately 0.05 torr) to remove both acetone and residual monomer. Approximately 1 milliliter of a solution was analyzed by both NMR and SEC revealing the solution was substantially free of trimer and higher oligomer. The solution comprises approximately 9% dimer formation and the remainder of the solution was substantially monomers.

The complete disclosures of all patents, patent applications, and publications are incorporated herein by reference as if individually incorporated. Various modifications and alterations of this invention will become apparent to those skilled in the art without departing from the scope and spirit of this invention, and it should be understood that this invention is not to be unduly limited to the illustrative embodiments set forth herein.

What is claimed is:

1. A process of making alpha-methylstyrene dimers comprising the steps of:
   a) adding a cobalt chain transfer catalyst, a-free-radical initiator and an alpha-methylstyrene monomer, in an inert atmosphere, to form a mixture;
   b) heating the mixture to a temperature in the range of 65° C. to 140° C.; and
   c) forming alpha-methylstyrene dimers and less than 0.1% by weight of 2,4-diphenyl-4-methyl-2-pentene.

2. The process according to claim 1, wherein the free-radical initiator is selected from the group consisting of azocumene; 2,2'-azobis(2-methyl)-butanenitrile; 2,2'-azobis(isobutyronitrile)(AIBN); 4,4'-azobis(4-cyanovaleric acid); 2-(t-butylazo)-2-cyanopropane; 1,1'-azobis(cyclohexane- 1 -carbonitrile), and combinations thereof.

3. The process according to claim 1, wherein the cobalt chain transfer catalyst is selected from the group consisting of a cobalt (II) chelate, cobalt (III) chelate and a combination thereof.

4. The process according to claim 3, wherein the cobalt catalyst comprises the general structure

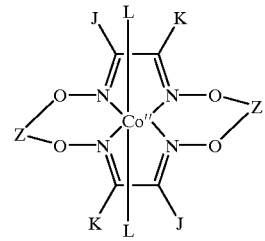

wherein Z is selected from the group consisting of hydrogen and $BR^{20}R^{21}$, where $R^{20}$ and $R^{21}$ are each independently selected from the group consisting of unsubstituted and substituted aryl, unsubstituted and substituted $C_1$–$C_{12}$ alkyl, unsubstituted and substituted $C_1$–$C_{12}$ alkoxy, unsubstituted and substituted aryloxy, and a halogen; J and K are each independently selected from the group consisting of phenyl, substituted phenyl, methyl, ethyl, and —$(CH_2)_4$—; and L is selected from the group consisting of water, an amine, an ammonia, a phosphine and combinations thereof.

5. The process according to claim 4 wherein Z is $BF_2$.

6. The process according to claim 4 wherein Z is selected from the group consisting of hydrogen and $BR^{20}R^{21}$, where $R^{20}$ and $R^{21}$ are each independently selected from the group consisting of unsubstituted and substituted aryl, unsubstituted and substituted $C^1$–$C_{12}$ alkyl, unsubstituted and substituted $C^1$–$C_{12}$ alkoxy, and unsubstituted and substituted aryloxy.

7. The process according to claim 3, wherein the cobalt catalyst comprises the general structure

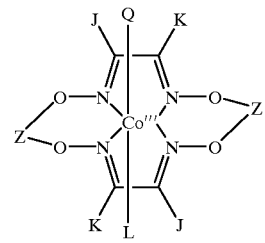

wherein Z is selected from the group consisting of hydrogen and $BR^{20}R^{21}$, where $R^{20}$ and $R^{21}$ are each independently selected from the group consisting of unsubstituted and substituted aryl, unsubstituted and substituted $C_1$–$C_{12}$ alkyl, unsubstituted and substituted $C_1$–$C_{12}$ alkoxy, unsubstituted and substituted aryloxy, and a halogen; J and K are each independently selected from the group consisting of phenyl, substituted phenyl, methyl, ethyl, and —$(CH_2)_4$—; L is selected from the group consisting of water, an amine, an ammonia, a phosphine and combinations thereof; and Q is an organic radical.

8. The process according to claim 7 wherein Z is $BF_2$.

9. The process according to claim 7 wherein Z is selected from the group consisting of hydrogen and $BR^{20}R^{21}$, where $R^{20}$ and $R^{21}$ are each independently selected from the group consisting of unsubstituted and substituted aryl, unsubstituted and substituted $C^1$–$C_{12}$ alkyl, unsubstituted and substituted $C^1$–$C_{12}$ alkoxy, and unsubstituted and substituted aryloxy.

10. The process according to claim 1, wherein the mixture of step b) is heated for at least 5 minutes.

11. The process according to claim 1, wherein the mixture of step b) is heated for approximately 10 hours to approximately 10 days.

12. The process according to claim 1, wherein the mixture of step b) is heated to a temperature in the range of 80° C. to 100° C.

13. The process according to claim 1, wherein in said step a), solvent is added with the cobalt chain transfer catalyst, the free radical initiator and the alpha-methylstyrene monomer to form a mixture.

14. A process of making alpha-methylstyrene dimers comprising the steps of:
   a) adding a cobalt chain transfer catalyst, a free-radical-initiator and an alpha-methylstyrene monomer, in an inert atmosphere, to form a mixture;
   b) heating the mixture to a temperature in the range of 65° C. to 140° C.; and
   c) forming a solution comprising greater than 20% by weight of alpha-methylstyrene dimers and having less than 0.1% by weight of 2,4-diphenyl-4-methyl-2-pentene.

15. The process according to claim 14, wherein a solvent is added with the cobalt catalyst, the free radical initiator and the alpha-methylstyrene monomer to form a mixture.

16. The process according to claim 14 further comprising a step of distilling the polymer solution of step c) to remove the alpha-methylstyrene monomer.

17. The process according to claim 14, wherein the free radical initiator is selected from the group consisting of azocumene; 2,2'-azobis (2-methyl)-butanenitrile; 2,2'-azobis (isobutyronitrile)(AIBN); 4,4'-azobis(4-cyanovaleric acid); 2-(t-butylazo)-2-cyanopropane; 1,1'-azobis(cyclohexane-1-carbonitrile), and combinations thereof.

18. The process according to claim 14, wherein the cobalt chain transfer catalyst is selected from the group consisting of cobalt (II) and cobalt (III) chelates and a mixture thereof.

19. The process according to claim 18, wherein the cobalt catalyst has the general structure

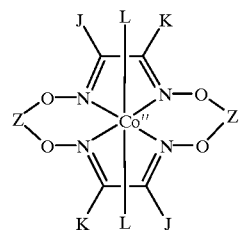

wherein Z is selected from the group consisting of hydrogen and $BR^{20}R^{21}$, where $R^{20}$ and $R^{21}$ are each independently selected from the group consisting of unsubstituted and substituted aryl, unsubstituted and substituted $C_1$–$C_{12}$ alkyl, unsubstituted and substituted $C_1$–$C_{12}$ alkoxy, unsubstituted and substituted aryloxy, and a halogen; J and K are each independently selected from the group consisting of phenyl, substituted phenyl, methyl, ethyl, and —$(CH_2)_4$—; and L is selected from the group consisting of water, an amine, an ammonia, a phosphine and combinations thereof.

20. The process according to claim 19 wherein Z is $BF_2$.

21. The process according to claim 18, wherein the cobalt catalyst has the general structure

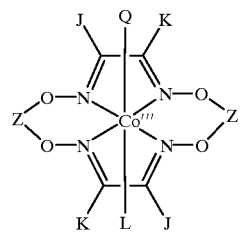

wherein Z is selected from the group consisting of hydrogen and $BR^{20}R^{21}$, where $R^{20}$ and $R^{21}$ are each independently selected from the group consisting of unsubstituted and substituted aryl, unsubstituted and substituted $C_1$–$C_{12}$ alkyl, unsubstituted and substituted $C_1$–$C_{12}$ alkoxy, unsubstituted and substituted aryloxy, and a halogen; J and K are each independently selected from the group consisting of phenyl, substituted phenyl, methyl, ethyl, and —$(CH_2)_4$—; L is selected from the group consisting of water, an amine, an ammonia, a phosphine and combinations thereof, and Q is an organic radical.

22. The process according to claim 21 wherein Z is $BF_2$.

23. The process according to claim 14, wherein the mixture of step b) is heated for approximately 10 hours to approximately 10 days.

24. The process according to claim 14, wherein the solution comprises greater than 50% by weight of alpha-methylstyrene dimer.

25. The process according to claim 14, wherein the mixture of step b) is heated to a temperature in the range of 80° C. to 100° C.

26. A process of making alpha-methylstyrene dimers comprising the steps of:
   a) adding a cobalt chain transfer catalyst, a free-radical initiator and an alpha-methylstyrene monomer, in an inert atmosphere, to form a mixture;
   b) initiating polymerization with an external source comprising ultraviolet light, visible light, electron beam or combinations thereof, and
   c) forming alpha-methylstyrene dimers and less than 0.1 % by weight of 2,4-diphenyl-4-methyl-2-pentene.

27. A process of making alpha-methylstyrene dimers comprising the steps of:
   a) adding a cobalt chain transfer catalyst selected from the group consisting of a cobalt (II) chelate, cobalt (III) chelate, and a combination thereof, a free-radical-initiator and an alpha-methylstyrene monomer, in an inert atmosphere, to form a mixture, wherein the cobalt (II) chelate comprises the general structure:

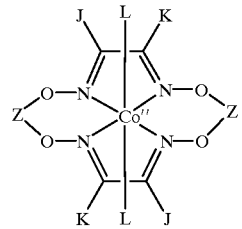

wherein Z is selected from the group consisting of hydrogen and $BR^{20}R^{21}$, where $R^{20}$ and $R^{21}$ are each independently selected from the group consisting of unsubstituted and substituted aryl, unsubstituted and substituted $C_1$–$C_{12}$ alkyl, unsubstituted and substituted $C_1$–$C_{12}$ alkoxy, unsubstituted and substituted aryloxy, and a halogen; J and K are each independently selected from the group consisting of phenyl, substituted phenyl, methyl, ethyl, and —$(CH_2)_4$—; and L is selected from the group consisting of water, an amine, an ammonia, a phosphine and combinations thereof; and wherein the cobalt (III) chelate comprises the general structure:

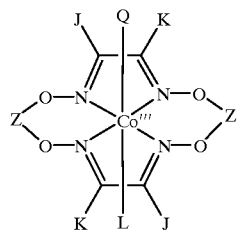

wherein Z is selected from the group consisting of hydrogen and $BR^{20}R^{21}$, where $R^{20}$ and $R^{21}$ are each independently selected from the group consisting of unsubstituted and substituted aryl, unsubstituted and substituted $C_1$–$C_{12}$ alkyl, unsubstituted and substituted $C_1$–$C_{12}$ alkoxy, unsubstituted and substituted aryloxy, and a halogen; J and K are each independently selected from the group consisting of phenyl, substituted phenyl, methyl, ethyl, and —$(CH_2)_4$—; L is selected from the group consisting of water, an amine, an ammonia, a phosphine and combinations thereof; and Q is an organic radical;

b) heating the mixture to a temperature in the range of 65° C. to 140° C.; and c) forming a solution comprising greater than 20% by weight of alpha-methylstyrene dimers and having less than 0.1% by weight of 2,4-diphenyl-4-methyl-2-pentene.

* * * * *